United States Patent [19]

Calamai et al.

[11] Patent Number: 4,508,643

[45] Date of Patent: Apr. 2, 1985

[54] RAT ANTIBODY TO HCG

[75] Inventors: Edward G. Calamai, Lexington; Martha A. Daigle, Brookline, both of Mass.

[73] Assignee: Baxter Travenol Laboratories, Inc., Deerfield, Ill.

[21] Appl. No.: 464,953

[22] Filed: Feb. 8, 1983

[51] Int. Cl.³ .................... C07G 7/00; A61K 39/44; A61K 39/395

[52] U.S. Cl. .................. 260/112 B; 424/85; 435/69; 435/172.2; 435/240; 435/241; 435/948; 426/547; 426/548

[58] Field of Search .......... 260/112 B; 424/85, 172.2; 435/69, 172, 948, 240, 241, 547, 548

[56] References Cited

U.S. PATENT DOCUMENTS

| | | | |
|---|---|---|---|
| 3,903,262 | 9/1975 | Pappenhagen et al. | 260/112 B X |
| 3,992,514 | 11/1976 | Donini | 260/112 B UX |
| 4,234,561 | 11/1980 | Bahl | 260/112 B X |
| 4,271,069 | 6/1981 | Tsong et al. | 260/112 SR |
| 4,350,683 | 9/1982 | Galfré et al. | 435/240 X |

FOREIGN PATENT DOCUMENTS

| | | | |
|---|---|---|---|
| 2500166 | 8/1982 | France . | |
| 2095831 | 10/1982 | United Kingdom | 435/172 |

OTHER PUBLICATIONS

Tawar et al., PNAS, U.S.A., vol. 72, 218–222, (1976).
Bahl et al., Biochem. Biophys. Res. Comm., vol. 70, 525–532, (1976).

*Primary Examiner*—Howard E. Schain

[57] ABSTRACT

Antibody against human chorionic gonadotropin is raised in rats, preferably Lewis Strain Inbred rats, using either whole hormone or the $\beta$-subunit as the antigen, and displays low cross-reactivity with luteinizing hormone as well as high sensitivity.

8 Claims, No Drawings

RAT ANTIBODY TO HCG

BACKGROUND OF THE INVENTION

1. Field of the Invention

This invention relates to the production of highly specific antibodies to human chorionic gonadotropin (hCG). These antibodies, produced in vivo by rats or in vitro by rat lymphocyte hybridomas, are useful in quantitating the levels of hormone in the blood of individuals as an indicator of pregnancy.

2. Description of the Prior Art

Chorionic gonadotropin is a hormone that is normally present in very low levels in the serum. Early in pregnancy the serum levels of hCG rise dramatically. This increase in hCG level can be measured by immunoassay procedures, which are the most common form of pregnancy test.

Commercially available immunoassays for hCG make use of either antisera from rabbits (polyclonal) or monoclonal antibodies derived from mouse hybridoma cells (Kohler and Milstein, Nature, Vol. 256, 495-7, 1975). For these assays to accurately measure hCG, the antibodies used in them must not cross react with other related hormones such as luteinizing hormone (LH), thyroid stimulating hormone (TSH), or follicle stimulating hormone (FSH). All four hormones have identical $\alpha$-subunits and similar $\beta$-subunits. As a result of the similarities, rabbits or mice immunized with intact, unmodified hCG molecules often produce antiserum (or in the case of mouse hybridomas, monoclonal antibodies) with unacceptably high cross-reactivity to the other hormones mentioned. When purified $\beta$-subunit of hCG is used for immunizations, as in Domini U.S. Pat. No. 3,992,514 or Tsong et al. U.S. Pat. No. 4,271,069, the animals still produce antibodies with significant cross-reactivity.

Alteration of the hCG molecule by conjugation to other molecules or by chemical means, as proposed by Tawar et al., PNAS, U.S.A., Vol. 72, 218-222 (1976); Bahl et al., Biochem. Biophys. Res. Comm., Vol. 70, 525-532 (1976); Pappenhagen et al. U.S. Pat. No. 3,903,262; or Bahl U.S. Pat. No. 4,234,561, often results in a molecule with reduced immunological activity yielding low titer, low affinity antibodies. In addition, these and other methods of hCG modification require significant technological effort and expense to produce an altered hCG molecule for immunization.

SUMMARY OF THE INVENTION

One feature of the invention is the production of antibodies to hCG which are highly sensitive and highly specific.

Another feature is the obtaining of these antibodies from serum or ascites fluid of rats immunized with whole, unmodified hCG.

Still another feature is the production of monoclonal antibodies of high specificity and sensitivity from whole, unmodified hCG.

It has been discovered that rats immunized with purified whole unmodified hCG (both $\alpha$- and $\beta$-subunits) or with the $\beta$-subunit alone differ from mice and rabbits in that they produce antiserum having little or no reactivity with human LH, and having affinity (sensitivity) characteristics that make it suitable for use in an immunoassay. Both inbred and outbred rat strains that are commercially available may be used, but rats of the Lewis Inbred Strain are preferred. Optionally, an ascites can be induced in these immunized animals; this ascites fluid contains antibodies with characteristics similar to the serum antibodies. The antibodies thus obtained are surprisingly superior to those obtained by the common practice of immunizing mammals such as mice or rabbits with whole, unmodified hCG. Alternatively, lymphocytes, e.g. splenocytes from the immunized rats can be fused with myeloma cells by conventional procedures to produce hybridoma cell lines. Clones of these hybridoma cells will produce monoclonal antibodies which can be selected for optimal sensitivity and low cross-reactivity and are remarkably better than monoclonal antibodies made from mice or rabbits immunized with whole hCG.

DETAILED DESCRIPTION

In practicing this invention, commercially available human chorionic gonadotropin can be used for the primary immunizing injection, as well as all subsequent boosts. For best results, the antigen should be of a relatively high degree of purity. The $\beta$-subunit can also be used with results superior to those obtained in other animals.

Rats of appropriate age are immunized with an antigen emulsion prepared by mixing equal amounts of hCG in normal saline with Freund's adjuvant. The emulsion is injected into the peritoneal cavity to elicit the immune antibody response. Although scheduling for injections may vary, a typical protocol would include a primary injection followed by an initial boost two weeks later. Additional boosts may be given at one month intervals.

Animals are generally bled seven to ten days after the most recent boost. Blood is removed from the rodent by severing the blood vessels of the tail. Generally, up to five milliliters of blood are removed at any time without the rat experiencing severe side effects. Serum is recovered by a two step method. Whole blood is allowed to coagulate at room temperature and blood serum is decanted. Removal of extraneous blood components is then completed by centrifugation and decantation.

As an alternative to the conventional antisera production described above, large volumes of ascitic fluid can be produced in rats. A suitable procedure involves the irritation of the peritoneal cavity of the immunized rats with a Freunds adjuvant emulsion, as described for example by Douglas et al., J.Immun.Methods, Vol. 26, 69-74 (1979), to induce formation of ascitic fluid having antibody activity closely approximating that of the serum.

Immune animals may also donate activated lymphocytes for cell fusion with commercially available mouse myeloma cells. Prior to the fusion procedure, animals are generally barraged with antigen preparations as described by Stahli et al., Immun.Methods, Vol. 32, 297-30, (1980). This treatment tends to increase the blast and plasma cell content in the lymphoid tissues. Cell fusion and hybridoma selection is carried out by the method of Kohler and Milstein, Nature, Vol. 256, 495-7 (1975). Tissue culture media supernatant is tested for antibody activity by an enzyme-linked immunosorbent assay (ELISA) as a preliminary screen, using commercially available reagents.

Antibody preparations from serum or ascitic fluid, and hybridoma cells, prepared as described above, are characterized for titer, sensitivity and percent cross-reactivity to human luteinizing hormone (LH) in a double antibody radioimmunoassay system (RIA).

Titer is defined as that dilution of sample which will bind thirty percent of total $^{125}$I-labeled hCG tracer. Antibody is diluted in a 2% (v/v) normal rat serum and salt buffer. A one hundred microliter aliquot of diluted antibody is allowed to react with an equal volume of $^{125}$I-tracer (approximately 2500 Ci/mmole activity). An inert calf serum aliquot is included in the system as a blank control. Precipitation is achieved with the addition of an appropriate anti-rodent immunoglobulin reagent. Reaction precipitates are recovered by centrifugation and decanting of supernatant.

Sensitivity of an antibody is determined by its ability to competitively inhibit hCG tracer binding when free, non-iodinated hCG is included in the system. Antibody preparations are generally described in terms of the midpoint of a standard concentration curve, or that amount of free hCG which will inhibit fifty percent of the calf serum blank value.

Percent cross-reactivity of an antibody to LH is determined at the same time as the sample sensitivity. Standard solutions of LH are prepared in the same fashion as the hCG standards. The percent cross-reactivity of a sample is calculated using the following formula:

$$\frac{\text{concentration of } hCG \text{ which inhibits 50\% of blank binding}}{\text{concentration of } LH \text{ which inhibits 50\% of blank binding}} \times 100 =$$

The rat antibodies of the present invention typically exhibit less than 15% cross-reactivity with LH, preferably less than 1%, while at the same time displaying high sensitivity to hCG with a midpoint hCG of 130 mIU/ml or less, preferably no more than 100 mIU/ml.

EXAMPLE 1

An antigenic emulsion composition was prepared by mixing equal amounts of Freund's adjuvant with a normal saline solution containing commercially available whole hCG. Equal amounts of the emulsion each containing approximately 50 μg of hCG were administered to a number of rats and mice by intraperitoneal injection, followed by three successive booster injections intraperitoneally and in all four footpads, the first booster two weeks after the initial injection and the remainder at monthly intervals thereafter. The animals were bled 7 to 10 days after the last boost, and serum recovered by coagulation, decantation, and centrifugation.

The antisera were then evaluated for titer, sensitivity (midpoint of standard concentration curve), and percent cross-reactivity to LH as described above, with the following results:

| SPECIES | STRAIN | TITER | MIDPOINT (hCG) | % CROSS REACTIVITY (LH) |
|---|---|---|---|---|
| MOUSE | C3H | 17.5K | 140 mIU/ml | 74% |
| " | C3H | 11K | 160 mIU/ml | 8% |
| " | C57B1/6 | 2.1K | 180 mIU/ml | 15% |
| " | C57B1/6 | 4.7K | 280 mIU/ml | 25% |
| RAT | BN | 21K | 100 mIU/ml | 7% |
| " | BN | 26K | 110 mIU/ml | 6% |
| " | Wistar | 17K | 125 mIU/ml | 8% |
| " | Wistar | 18.5K | 120 mIU/ml | 34% |
| " | SD | 14.5K | 96 mIU/ml | 8% |
| " | SD | 17K | 115 mIU/ml | 6% |
| " | Lewis | 1.9K | 70 mIU/ml | 2% |

EXAMPLE 2

The procedure described in Example 1 was followed except that a fourth boost was added after a one-month interval, followed by bleeding after 7–10 days, with the following results:

| SPECIES | STRAIN | TITER | MIDPOINT (hCG) | % CROSS REACTIVITY (LH) |
|---|---|---|---|---|
| RAT | Lewis | 100 | 98 mIU/ml | 3.2% |
| " | " | 35K | 40 mIU/ml | 2.22% |
| " | " | 10K | 70 mIU/ml | 2.3% |
| " | " | 450 | 100 mIU/ml | <1.0% |
| MOUSE | C3H | 29K | 64 mIU/ml | 134% |
| " | " | 6.2K | 70 mIU/ml | 100% |
| " | " | 11K | 100 mIU/ml | 71.4% |
| " | " | 35K | 45 mIU/ml | 100% |

EXAMPLE 3

The same procedure was followed as in Example 2 except that purified β-subunit hCG was substituted for whole hCG for each booster injection, with the following results:

| SPECIES | STRAIN | TITER | MIDPOINT (hCG) | % CROSS REACTIVITY (LH) |
|---|---|---|---|---|
| RAT | Lewis | 6.4K | 66 mIU/ml | 1.7% |
| " | " | 4.5K | 80 mIU/ml | <0.8% |
| " | " | 4.7K | 94 mIU/ml | <0.94% |
| " | " | 3.7K | 94 mIU/ml | 2.08% |
| MOUSE | C3H | 35K | 60 mIU/ml | 100% |
| " | " | 7K | 140 mIU/ml | 29% |
| " | " | 4.5K | 190 mIU/ml | 70% |
| " | " | 7K | 80 mIU/ml | 100% |

EXAMPLE 4

The procedure of Example 2 was followed except that only rats were employed, and after the last booster injection each animal was induced to form an ascites by irritation of the peritoneal cavity with a Freund's adjuvant emulsuion over a period of 12 days following the procedure of Douglas et al., J.Immun.Methods, Vol. 26, 69–74 (1979). Each animal was then bled from the tail vein at the same time as drainage of the ascites. Both the blood serum and the ascites fluid were then assayed with the following results (cross-reactivity is against LH):

| | ASCITES | | | | SERUM | | |
|---|---|---|---|---|---|---|---|
| STRAIN | VOLUME | TITER | MIDPOINT | % CROSS REACT. | TITER | MIDPOINT | % CROSS REACT. |
| BN | 52 ml | 9.6K | 82 mIU/ml | 11% | 18K | 70 mIU/ml | 12% |

-continued

| STRAIN | ASCITES | | | | SERUM | | |
|---|---|---|---|---|---|---|---|
| | VOLUME | TITER | MIDPOINT | % CROSS REACT. | TITER | MIDPOINT | % CROSS REACT. |
| BN | 94 ml | 18K | 82 mIU/ml | 9% | 25K | 80 mIU/ml | 11% |
| BN | 93 ml | 27K | 100 mIU/ml | 5% | 37K | 100 mIU/ml | 10% |
| Wistar | 45 ml | 7K | 130 mIU/ml | 11% | 11K | 120 mIU/ml | 12% |
| Wistar | 33 ml | 29K | 80 mIU/ml | 10% | 40K | 78 mIU/ml | 9% |
| SD | 38 ml | 12K | 110 mIU/ml | 22% | 14K | 98 mIU/ml | 19% |
| Lewis | 15 ml | 9K | 70 mIU/ml | 2% | 14K | 66 mIU/ml | 2% |
| Lewis | 67 ml | 5K | 60 mIU/ml | 6% | 7K | 80 mIU/ml | 5% |

EXAMPLE 5

The procedure of Example 1 was employed to immunize a rat (Strain Wistar) and a mouse (Strain Balb/c). Each animal was barraged with the antigenic emulsion by the procedure of Stahli et al., supra, and was sacrificed approximately 3 days after the last injection, and the rat lymph node cells fused to generally available mouse myeloma cell line P3X63Ag8-653 by conventional procedures as described by Kohler and Milstein, supra. The mouse was splenectomized and the spleen cells fused with the generally available mouse myeloma cell line SP 2/0. The resulting hybridomas in each case were cultured and screened for anti-hCG antibody production by an enzyme-linked immunosorbent assay of the supernatant culture medium. Cloning of selected hybridomas from each animal was achieved by limiting dilution in the tissue culture system, and the monoclonal antibody from each was characterized by standard radioimmunoassay, with the following results (cross-reactivity is against LH):

| HYBRID | CLONE | MAXIMUM ASSAY BINDING | MIDPOINT (hCG) | % CROSS REACTIVITY |
|---|---|---|---|---|
| RAT × MOUSE | 5D2 | 13% | 50 mIU/ml | 2.5% |
| MOUSE × MOUSE | 18D9G1 | 15% | 155 mIU/ml | <1.0% |

As can be seen, the rat×mouse monoclonal antibody displayed a combination of high sensitivity with low cross-reactivity.

In addition, the rat×mouse hybridoma cells are effective to produce ascites fluid when injected into athymic (immunoincompetent) mice; this ascites fluid exhibits hCG antibody activity similar to that of the supernatant tissue culture medium in which the hybridomas were grown in vitro, and is useful in the same way.

EXAMPLE 6

Rabbits (New Zealand White) were immunized with initial intradermal injections at 40 sites with a total of 50 μg of whole hCG, followed by four subcutaneous boosts of whole hCG (10-20 sites each), then bled. The rabbit antiserum was assayed in the same manner as the antisera of Example 1, with the following results:

| RABBIT | TITER | MIDPT (hCG) | % CROSS REACTIVITY (LH) |
|---|---|---|---|
| 198 | 22K | 115 mIU/ml | 100% |
| 206 | 14K | 78 mIU/ml | 100% |
| 208 | 17K | 115 mIU/ml | 100% |
| 210 | 25K | 80 mIU/ml | 100% |

In general, 90% of rabbits injected with whole hCG give antisera with high cross reactivity to LH.

The present invention makes it unnecessary to dissociate whole hCG into the α- and β-subunits, since the whole hormone containing both subunits can be used for raising the desired antibody; it also eliminates any need for absorbing or reacting the antibody with α-subunit hCG or otherwise altering it in order to obtain anti-hCG antibody of high sensitivity and low cross-reactivity to LH.

What is claimed is:

1. The method of raising anti-hCG antibody of high sensitivity and low cross-reactivity with LH which comprises administering whole hCG or β-subunit thereof to a rat, and harvesting anti-hCG antibody from said rat.

2. A method as claimed in claim 1 in which whole hCG is administered.

3. A method as claimed in claim 1 in which said rat is Lewis Strain Inbred.

4. A method as claimed in claim 2 in which said rat is Lewis Strain Inbred.

5. Rat antibody of high sensitivity which is anti-hCG and which has low cross-reactivity with LH.

6. Rat antibody as claimed in claim 5 which is in the form of antiserum.

7. Rat antibody as claimed in claim 5 which is in the form of ascites fluid.

8. Rat antibody as claimed in claim 5 which is in the form of monoclonal antibody.

* * * * *